United States Patent [19]

Roberts

[11] Patent Number: 5,008,432
[45] Date of Patent: Apr. 16, 1991

[54] PRODUCTION OF MERCAPTO COMPOUNDS

[75] Inventor: John S. Roberts, Bartlesville, Okla.

[73] Assignee: Phillips Petroleum Company, Bartlesville, Okla.

[21] Appl. No.: 754,058

[22] Filed: Jul. 11, 1985

[51] Int. Cl.$^5$ .................. C07C 319/04; C07C 323/03; C07C 323/41; C07C 323/60

[52] U.S. Cl. .................................. 558/436; 260/399; 560/147; 560/154; 562/512; 564/192; 568/36; 568/62; 568/63

[58] Field of Search ................ 560/147, 154; 260/399, 260/465.1; 568/36, 41, 62, 63, 72; 564/192; 562/512; 558/436

[56] References Cited

U.S. PATENT DOCUMENTS

| 2,268,185 | 12/1941 | Burke et al. | 560/147 |
| 4,052,440 | 10/1977 | Gladstone et al. | 560/147 |
| 4,067,901 | 1/1977 | Gladstone et al. | 560/147 |
| 4,232,167 | 11/1980 | Louthan | 560/154 |
| 4,307,225 | 12/1981 | Louthan | 528/274 |
| 4,433,134 | 2/1984 | Louthan | 528/279 |

FOREIGN PATENT DOCUMENTS 82-48155 10/1982 Japan .

Primary Examiner—Vivian Garner
Attorney, Agent, or Firm—A. W. Umphlett

[57] ABSTRACT

Activated olefinically unsaturated organic compounds such as esters, acids, ketones, nitriles, and the like, are reacted with hydrogen sulfide in the presence of at least one of magnesium oxide and anion exchange resins catalysts to produce saturated sulfur-containing compounds. In a specific embodiment, unsaturated carboxylates are converted in high yields to mercaptoalkanoates.

5 Claims, No Drawings

PRODUCTION OF MERCAPTO COMPOUNDS

BACKGROUND OF THE INVENTION

This invention relates to the preparation of organic sulfur compounds. In another aspect, this invention relates to the reaction of unsaturated organic materials, i.e. olefins in which the double bond is conjugated with an activating group such as carbonyl, carboxyl, carboxamide, nitrile, nitro, sulfoxide, and the like in the presence of selected catalysts under high pressure liquid phase conditions. In still another aspect, this invention relates to improved catalyst and process conditions for increasing product yield from unsaturated organic materials. It further relates to a method of preparing alkyl mercaptoalkanoates.

The reaction of hydrogen sulfide with olefinically unsaturated organic compounds is an important process for the production of organic sulfur compounds which are intermediates in the production of compositions having a variety of commercial uses. For example, the reaction of $H_2S$ with olefinically unsaturated carboxylate in the presence of a catalyst is a known method of preparing alkyl mercaptoalkanoates along with varying amounts of other organic sulfur compounds. Some of the catalysts that are known in the art are fairly effective and offer commercial potential. However, many are either too expensive or not particularly active for high conversion of the carboxylate to the desired mercaptoalkanoate. The present invention relates to improved catalyst systems and process conditions useful for the conversion of olefinically unsaturated carboxylates, esters, and other activated unsaturated organic compounds in high yields to desired organic sulfur-containing products.

Accordingly, an object of this invention is to provide an improved process for preparing alkyl mercaptoalkanoates.

Another object of this invention is to provide catalysts active for the conversion of olefinically unsaturated carboxylates to alkyl mercaptoalkanoates.

Another object is to provide improved process and catalysts for conversion of activated unsaturated organic compounds.

Other objects, aspects as well as the several advantages of the invention will be apparent to those skilled in the art upon reading the specification and the appended claims.

SUMMARY OF THE INVENTION

Broadly, according to the invention, a process is provided for the conversion of activated unsaturated organic compounds in high yields to desired sulfur-containing products by carrying out the reaction of $H_2S$ with an activated unsaturated organic compound in the presence of selected catalysts and/or under specific reaction conditions.

In accordance with the invention, activated ethylenically unsaturated organic compounds, wherein the double bond is conjugated with an activating group such as carbonyl, carboxyl, carboxamide, nitrile, nitro, sulfoxide, or other like groups, are reacted with $H_2S$ in the presence of a magnesium oxide catalyst or an ion exchange resin catalyst under elevated conditions of pressure sufficient to maintain liquid phase conditions.

In accordance with one embodiment of this invention, olefinically unsaturated carboxylates are reacted with $H_2S$ in the presence of magnesium oxide catalysts under reaction conditions which produce alkyl mercaptoalkanoates.

In a more specific embodiment of the invention, methyl acrylate is reacted with $H_2S$ in the presence of magnesium oxide or anion exchange resin catalysts under conditions which produce methyl 3-mercaptopropionate in high yields and high selectivity to the desired product.

DETAILED DESCRIPTION OF THE INVENTION

The instant invention is broadly applicable to activated olefinically unsaturated compounds including unsaturated esters, unsaturated acids, unsaturated ketones, unsaturated nitriles, and the like. Specific examples of these include dimethyl maleate, acrylic acid, methyl vinyl ketone, acrylonitrile, and the like.

The olefinically unsaturated esters, especially the carboxylates, suitable for use in the process of the invention are those materials represented by the formula $$CR_2 = CRCO_2R'$$

wherein R' is an alkyl radical having 1 to 5 carbon atoms; each R is selected independently from H and R'; and the total number of carbon atoms in all the R groups does not exceed about 15 carbon atoms per molecule.

Materials represented by this formula are, for example, methyl acrylate, ethyl acrylate, methyl methacrylate, ethyl 2-butenoate, n-butyl 2-hexenoate, and t-butyl 2-methyl-2-heptenoate, and the like and mixtures thereof. Methyl acrylate is the presently preferred unsaturated carboxylate.

The alkyl mercaptoalkanoates which can be produced by the catalyzed addition reaction can be represented by the formula $$HS\ CR_2\ CHR\ CO_2R'$$

wherein R' is an alkyl radical having 1 to 5 carbon atoms; each R is selected independently from H and R'; and the total number of carbon atoms in the R groups does not exceed about 15 carbon atoms per molecule.

Examples of alkyl mercaptocarboxylates represented by this formula include methyl 3-mercaptopropionate, ethyl 3-mercaptobutyrate, n-butyl 3-mercaptohexanoate, isopropyl 3-mercaptopropionate, n-pentyl 3-mercaptopropionate, methyl 3-mercaptomethylpropionate, 3-mercapto-2-methylbutyrate, and the like and mixtures thereof.

Hydrogen sulfide is generally present in an amount of 0.5 to 10 moles of $H_2S$ per mole of activated unsaturated organic compound, preferably 3 to 8 moles $H_2S$ per mole of compound.

One catalyst useful in the process of this invention is magnesium oxide which can be combined with an inorganic metal oxide compound, such as silica, alumina, silica-alumina and the like, which may function as binders. Magnesium oxide is a known material and can be prepared by methods known in the art.

Other catalysts that can be used according to the invention include weakly basic anion exchange resins. The anion exchange resins used according to the invention as catalysts can include a variety of weakly basic anion exchange resins particularly those containing tertiary amines as functional groups and those containing quaternary ammonium hydroxides as functional groups. Anion exchange resins are known in the art and comprise insoluble anion exchange resins having crosslinked polymer base. The base used as the foundation for these anion exchange resins are polymers, such as polystyrene, polyacrylamide and epoxy resins rendered insoluble by crosslinking. Specifically, the anion exchange resins that can be used according to the invention include the following products:

Amberlyst A-21 (Rohm and Haas)
Amberlyst A-26 (Rohm and Haas)

It is within the scope of the invention to use mixtures of these as well as other anion exchange resins.

The addition of hydrogen sulfide to activated olefinically unsaturated compounds can be carried out in the presence or absence of diluents. Suitable diluents that can be used include lower alcohols as well as saturated aliphatic, saturated cycloaliphatic or aromatic hydrocarbons. Examples of suitable diluents include methanol, ethanol, isopropanol, pentane, hexane, isooctane, cyclohexane, benzene, toluene, the xylenes, and the like, and mixtures thereof.

The addition of hydrogen sulfide to activated olefically unsaturated organic compounds is conducted under whatever conditions of temperature, pressure and time are desirable to achieve the desired results when using magnesium oxide as the catalyst. Temperatures in the range of about 25° to about 150° C. are generally suitable for the reaction; however, because of the exothermic nature of the reaction, it may be desirable to provide external cooling to the reactor. The pressure under which the reaction is generally carried out is in the range of about 200 to about 2000 psig (1350 to 13,500 kPa), preferably about 200 to about 500 psig (1350 to 3450 kPa). The conditions of pressure during the reaction when using anion exchange resin catalysts will ordinarily be higher than described above with respect to use of magnesium oxide catalysts. The pressure will ordinarily be at least about 400 psig so that a significant amount of $H_2S$ will be in the liquid phase during the reaction. Generally, the pressure will be in the range of 450 to 1,000 psig if an anion exchange resin is used as the catalyst.

In continuous operation, the flow rate of reaction mixture, i.e. activated unsaturated organic compound and $H_2S$, through magnesium oxide catalyst will range from about 1 to about 10 liquid hourly space velocity (LHSV), preferably about 6 to about 8 LHSV.

Following reaction of hydrogen sulfide with olefinically unsaturated carboxylate, for example, it is desirable to remove the volatile diluent, unreacted starting materials and volatile by-products. This is readily accomplished by flashing the undesired volatile components from the reaction mixture. The resulting residue is primarily an alkyl mercaptoalkanoate and dialkyl thiodialkanoate but small amounts of other sulfur compounds can be obtained if oxygen is not carefully excluded from the reaction. An advantage of this process is that the conversions are essentially quantitative, thus avoiding the problem of residual acrylate, for example, which tends to polymerize in the column on distillation.

The following Example represents one presently preferred embodiment of the invention.

EXAMPLE I

Addition of H₂S to Methyl Acrylate

Methyl acrylate for each experiment is placed in a glass reservoir. The hydrogen sulfide is stored in a Hoke stainless steel, 2-litre cylinder which is pressurized with nitrogen to maintain the hydrogen sulfide in the liquid state. The cylinder is fitted with a calibrated sight glass to permit visual following of the use of the hydrogen sulfide. A Milton Roy Duplex Pump is used to meter and pump the methyl acrylate and hydrogen sulfide simultaneously. The two reactants are mixed after leaving the pump and before entering the 20-inch long, one-inch diameter stainless steel reactor containing the catalyst. The catalyst is a granular magnesium oxide (12-20 mesh) (Dart Industries, now Catalyst Resources, Inc., 555 Garden Street, Elyria, Ohio 44036) containing about 5% silica as a binder. On exiting the reactor the reaction product mixture is passed through a Moore flow controller which maintains the desired pressure in the reactor. The reaction is exothermic and on larger scale reactions will require cooling to remove the excess heat.

The product mixture is collected as it passes through the Moore flow controller and the excess hydrogen sulfide is removed as the pressure is reduced to atmospheric, optionally heat is applied to maintain the temperature at 40-50° C. to assist in the removal of the hydrogen sulfide which is now available for recycle to the reactor.

On distillation methyl 3-mercaptopropionate distills at 68–70° C./15 mm and dimethyl 3,3'-thiodipropionate distills at 165-169° C./15 mm. If oxygen is not carefully excluded, there will be formed also some dimethyl 3,3'-dithiodipropionate which distills at 178-184° C./10 mm. Results of a number of runs using this procedure are shown in Table 1.

TABLE I

Preparation of Methyl 3-Mercaptopropionate (MMP) Using MgO Catalyst-MgO with 5% Silica Binder
Pressure - 450 psig
Conversion - 100%

| Run No. | Temperature, °C. Preheat | Bed | Selectivity to MMP |
|---|---|---|---|
| (LHSV = 6.96/hr; H₂S/MA = 7.34) MA = Methyl Acrylate |
| 1 | 33 | 99 | 8 |
| 2 | 39 | 58 | 73 |
| 3 | 46 | 60 | 88 |
| 4 | 47 | 61 | 89 |
| 5 | 48 | 61 | 89 |
| 6 | 48 | 61 | 88 |
| (LHSV = 7.08/hr; H₂S/MA = 7.50) |
| 7 | 27 | 56 | 95.6 |
| 8 | 30 | 58 | 95.8 |
| 9 | 31 | 58 | 94.8 |
| 10 | 31 | 58 | 95.4 |
| 11 | 32 | 58 | 94.2 |
| 12 | 27 | 56 | 94.1 |
| 13 | 28 | 56 | 95.4 |
| 14 | 28 | 56 | 96.6 |
| (LHSV = 7.08/hr; H₂S/MA = 7.50 |
| 15 | 27 | 56 | 96.8 |
| 16 | 24 | 56 | 93.0 |
| 17 | 25 | 57 | 92.9 |
| 18 | 25 | 57 | 93.4 |
| 19 | 30 | 59 | 91 |
| 20 | 29 | 60 | 91 |
| 21 | 29 | 61 | 90 |
| (LHSV = 7.08/hr; H₂S/MA = 7.50) |
| 22 | 25 | 57 | 93.9 |
| 23 | 26 | 58 | 93.5 |
| 24 | 27 | 57 | 94.3 |
| 25 | 30 | 57 | 93.6 |
| 26 | 24 | 54 | 96.3 |
| 27 | 27 | 56 | 94.0 |
| 28 | 28 | 58 | 93.0 |

It is seen that good conversion and selectivity to the desired methyl 3-mercaptopropionate are obtained with the magnesium oxide catalyst and that it is advantageous to keep the preheat temperature fairly low.

If the hydrogen sulfide has been moved in the liquid phase from its shipping container, it will often contain an iron impurity which interferes with the activity of the magnesium as it is shown in Table II.

TABLE II

Preparation of Methyl 3-Mercaptopropionate (MMP)
$H_2S$ Fed from Cylinder in Liquid Phase
Catalyst MgO
Pressure - 450 psig

| Run No. | LHSV hr$^{-1}$ | $H_2S$/MA | Temperature., °C. Preheat | Bed | Conversion % | Selectivity to MMP |
|---|---|---|---|---|---|---|
| 29 | 10.1 | 7.76 | 24 | 56 | 100 | 88.0 |
| 30 | 6.96 | 8.12 | 23 | 38 | 85 | 75.0 |
| 31 | 6.96 | 8.12 | 23 | 40 | 87 | 79.0 |

This problem is avoided by distilling the hydrogen sulfide, which is readily accomplished by removing the $H_2S$ from the cylinder in the gaseous phase.

EXAMPLE II

Methyl Mercaptopropionate Using Anion Exchange Catalyst

The reactor and the procedure were the same as in Example I except that the catalyst was Amberlyst A-21 (Rohm and Haas), a weakly basic macroreticular ion exchange resin consisting mainly of dimethylamino groups on a polystyrene/divinylbenzene copolymer. No heat was added in the preheat section. A temperature gradient which developed throughout the bed reached a maximum generally in the range of about 70° C. to 115° C. at a distance of about 50 to 75% of the length of the catalyst bed as the space velocity (LHSV) of the total reaction mixture was varied from about 10 hr$^{-1}$ to about 20 hr$^{-1}$. Samples were taken at about 30 minute intervals and analyzed by glc. A total reactant space velocities greater than about 15 hr$^{-1}$ the yield of the desired mercaptan is seen to decline.

TABLE III

Addition of $H_2S$ To Methyl Acrylate (MA) Using
An Anion Exchange Resin Catalyst
Catalyst: Amberlyst* A-21 (25 ml)
Pressure: 450 psig
Preheat: None

| Length of Run hrs | Methyl Acrylate LHSV (hr$^{-1}$) | Hydrogen Sulfide LHSV (hr$^{-1}$) | $H_2S$/MA Mole Ratio | Bed$^a$ Temp. °C. | Conversion (% of MA) | Selectivity to MMP (%) |
|---|---|---|---|---|---|---|
| 0.5 | 2.88 | 8.14 | 5.9 | 100 | 100 | 88.9$^b$ |
| 1.5 | 2.95 | 6.67 | 4.8 | 84 | 100 | 94.8$^c$ |
| 3.0 | 2.95 | 7.20 | 5.2 | 84 | 100 | 95.3$^d$ |
| 1.5 | 2.83 | 8.45 | 6.3 | 73 | 100 | 97.3$^c$ |
| 1.0 | 3.74 | 8.45 | 4.8 | 98 | 100 | 93.1$^e$ |
| 2.0 | 3.74 | 10.85 | 6.14 | 84 | 100 | 95.3$^f$ |
| 1.0 | 5.02 | 10.68 | 4.5 | 111 | 100 | 79.9$^e$ |
| 1.5 | 5.02 | 14.4 | 6.1 | 78 | 94.2 | 88.0$^c$ |

$^a$Highest temperature reached in a set of samples
$^b$One sample
$^c$average of three samples
$^d$average of six samples
$^e$average of two samples
$^f$average of four samples
*Amberlyst is a tradename of Rohm and Haas Company. Amberlyst A-21 is a weakly basic ion exchange resin consisting of dimethylamino groups on polystyrene/divinyl benzene copolymer.

(e) average of two samples (f) average of four samples * Amberlyst is a tradename of Rohm and Haas Company. Amberlyst A-21 is a weakly basic ion exchange resin consisting of dimethylamino groups on polystyrene/-divinyl benzene copolymer.

EXAMPLE III

Methyl Mercaptopropionate Using Mixed Anion Exchange Catalyst

The reactor and procedure were the same as in Example I except that the catalyst consisted of a mixture of 50 mL of Amberlyst A-21 and 15 mL of Amberlyst A-26 (Rohm and Haas), consisting mainly of trimethylammonium chloride groups on a backbone of polystyrene/divinylbenzene, and the mole ratio of $H_2S$ to methyl acrylate was maintained at 6:1. The pressure was maintained at 450 psi. Run times were about 30 minutes each. The flow rates were maintained at 1.4 mL/min for methyl acrylate and 4.5 mL/min. for hydrogen sulfide. Conversion was essentially 100% in each instance.

TABLE IV

Addition of $H_2S$ to Methyl Acrylate Using
Mixed Anion Exchange Resin Catalyst

| Run No. | Preheat Temp. °C. | Hot Spot Temp. °C. | Selectivity % to MMP | MMP/Sulfide |
|---|---|---|---|---|
| 1 | 93 | 61 | 97.8 | 43.5 |
| 2 | 74 | 73 | 96.3 | 26.2 |
| 3 | 73 | 66 | 97.2 | 34.0 |
| 4 | 74 | 67 | 96.9 | 31.7 |
| 5 | 74 | 66 | 97.2 | 34.0 |
| 6 | 75 | 66 | 97.3 | 35.3 |

EXAMPLE IV

Advantages of Using Higher Pressure and No Additional Solvent

The advantage of the use of higher pressure and no additional solvent were demonstrated in comparable experiments. Operation at higher pressures (450 psig and greater) provided a degree of liquefaction of the hydrogen sulfide that was beneficial in causing it to function as a solvent for the reaction. Under these conditions the hydrogen sulfide also absorbs much of the heat of reaction by gasifying, thus functioning as a heat sink and moderating the reaction temperature. Calculations indicate that even at the upper temperature of 85° C. and at 450 psi approximately 15% of the $H_2S$ is in the liquid state. These conditions permit a more rapid reaction than is possible in the presence of other solvents, such as dimethyl thiodipropionate, dimethyl polythiodipropionate or reaction mixture, and produces surprisingly high selectivity to the monoadduct, methyl 3-mercaptopropionate, with very little of the diadduct, dimethyl 3,3'-thiodipropionate.

TABLE V

Comparison of Invention With Previous Process Using Anion Exchange Resin Catalyst

|  | Present Invention | Process Run According to Jap. Pat. J 82 048155 | |
|---|---|---|---|
|  |  | Run 1 | Run 2 |
| LHSV, $H_2S$, hr$^{-1}$ | 10.8 | 11.4 | 11.4 |
| LHSV, Methyl acrylate (MA), hr$^{-1}$ | 3.74 | 3.42 | 3.42 |
| Pressure, psig | 450 | 280 | 280 |
| $H_2S$/MA | 6.1 | 6 | 6 |
| Added Solvent, DMTD[a], % based on MA | 0 | 10 | 10 |
| Conversion, % | 100 | 89.2 | 100 |
| Selectivity to Monoadduct, MMP, % | 95.3 | 74.5 | 73.7 |

[a]DMTD = Dimethyl 3,3'-thiodipropionate
[b]Two runs made

Comparison of the data show that the use of the higher pressure and no additional solvent results in a significant improvement in the selectivity to and yield of the methyl mercaptopropionate.

EXAMPLE V

Reaction of Methyl Acrylate (MA) and Hydrogen Sulfide at Lower Pressure

A further run was made at the lower pressure without the added dimethyl thiodipropionate (DMTD) as additional solvent.

Gaseous hydrogen sulfide was depressured to 280 psig through a metering valve and rotameter and after mixing with methyl acrylate was passed through a tubular stainless steel reactor containing Amberlyst A-21 (Rohm and Haas) catalyst (25 mL) followed by about 50 mL of glass beads (5 mm). A Moore flow controller maintained the system pressure at 280 psig while letting the product mixture exit to atmospheric pressure. Grab samples were taken at 30 minute intervals and analyzed by glc.

TABLE VI $H_2S$ Addition to Methyl Acrylate at Lower Pressure
Pressure: 280 psig
$H_2S$/MA, mole ratio: 6.1

| Run No. | Mid-Bed Temp. (°C.) | Conversion (%) | Selectivity | |
|---|---|---|---|---|
|  |  |  | MMP | Sulfide |
| 1 | 97 | 99.5 | 74.5 | 25.5 |
| 2 | 106 | 100.0 | 70.3 | 29.7 |
| 3 | 89 | 100.0 | 70.5 | 29.5 |
| 4 | 85 | 99.8 | 76.8 | 23.2 |
| 5 | 91 | 99.8 | 75.9 | 24.1 |
| 6[b] | 116 | 99.8 | 71.5 | 28.5 |
| 7[b] | 60 | 98.5 | 83.0 | 17.0 |
| 8 | 75 | 99.5 | 79.8 | 20.2 |
| 9 | 62 | 99.5 | 83.7 | 16.1 |
| 10 | 68 | 99.7 | 83.3 | 16.7 |
| 11 | 76 | 99.7 | 80.4 | 19.3 |

EXAMPLE VI

Preparation of Dimethyl Mercaptosuccinate

The apparatus and the procedure were the same as those used in Example II except that dimethyl maleate was used instead of methyl acrylate. The pressure was maintained at 450 psig and the conversion was essentially 100% in each instance.

TABLE VII

Preparation of Dimethyl Mercaptosuccinate
Pressure: 450 psig
Conversion: 100%

| Run No. | Mid-Bed Temp. °C. | LHSV (hr$^{-1}$) | $H_2S$/Maleate Molar Ratio | Selectivity to Succinate |
|---|---|---|---|---|
| 1 | 62 | 7.2 | 5.89 | 67.0 |
| 2 | 62 | 7.2 | 5.89 | 81.0 |
| 3 | 63 | 7.2 | 5.89 | 70.4 |
| 4 | 62 | 7.2 | 5.89 | 78.4 |
| 5 | 61 | 7.2 | 5.89 | 70.6 |
| 6 | 66 | 7.2 | 5.89 | 64.2 |
| 7 | 62 | 7.2 | 5.89 | 53.4 |
| 8 | 65 | 7.2 | 5.89 | 73.3 |
| 9 | 63 | 7.2 | 5.89 | 72.7 |
| 10 | 63 | 7.2 | 5.89 | 73.4 |
| 11 | 67 | 7.2 | 5.89 | 73.5 |
| 12 | 59 | 6.7 | 7.55 | 84.1 |
| 13 | 66 | 6.7 | 7.55 | 83.1 |
| 14 | 73 | 6.7 | 7.55 | 75.8 |
| 15 | 61 | 6.7 | 7.55 | 65.7 |
| 16 | 71 | 6.7 | 7.55 | 64.0 |
| 17 | 59 | 6.7 | 7.55 | 66.8 |
| 18 | 62 | 6.7 | 7.55 | 75.1 |
| 19 | 50 | 6.7 | 7.55 | 67.6 |
| 20 | 51 | 6.7 | 7.55 | 81.1 |
| 21 | 50 | 6.7 | 7.55 | 72.3 |
| 22 | 50 | 6.7 | 7.55 | 72.4 |
| 23 | 51 | 6.7 | 7.55 | 72.5 |
| 24 | 53 | 6.7 | 7.55 | 72.4 |

Under the conditions of this process, selectivity to the monoadduct is acceptable but somewhat lower with the second activating carboxylate group present, which results in a "cross-conjugation" and thus reducing the activation of the olefin.

EXAMPLE VII

Addition of $H_2S$ to Acrylic Acid

The reaction worked surprisingly well with the acrylic acid itself. There was some interaction with the weakly basic catalyst and a small amount of solid was formed. The solid contained mercaptan and sulfide linkages as well as acrylic acid and dimers and trimers thereof, but was not analyzed further. The reaction was somewhat slower initially but built up to an acceptable level in about four hours. The reaction and procedure were the same as in Example II except that acrylic acid was used instead of methyl acrylate.

TABLE VIII

Addition of $H_2S$ to Acrylic Acid
Pressure: 450 psig

| Sample No. | Total Run Time, Hrs. | Mid-Bed Temp. °C. | LHSV (hr$^{-1}$) | $H_2S$/Acid Mole Ratio | Conv. % | Selectivity, % to Monoadduct |
|---|---|---|---|---|---|---|
| 1 | 2 | 42 | 9.67 | 5.4 | 51 | 100 |
| 2 | 3 | 39 | 9.67 | 5.4 | 70 | 100 |
| 3 | 4 | 41 | 9.67 | 5.4 | 90 | 98 |
| Shut down about 43 hours. Restarted. | | | | | | |
| 4 | 3.5 | 44 | 4.87 | 10.4 | 89 | 100 |

EXAMPLE VIII

Addition of $H_2S$ to Methyl Vinyl Ketone (2-Butenone)

The applicability of this process to other activated olefins is demonstrated by the addition of hydrogen sulfide to methyl vinyl ketone (3-buten-2-one). The apparatus and procedure is the same as in Example II except that methyl vinyl ketone was used in instead of methyl acrylate.

TABLE IX

Preparation of 4-Mercapto-2-butanone
Pressure: 450 psi
H$_2$S/Ketone, mole ratio: 6.03
LHSV, hr$^{-1}$: 6.36
Conversion: 100%

| Sample No. | Total Run Time Hrs. | Mid-Bed Temp. °C. | Selectivity to Mercaptan |
|---|---|---|---|
| 1 | 1 | 51 | 100 |
| 2 | 1.75 | 52 | 90.8 |
| 3 | 2.25 | 54 | 91.2 |
| 4 | 2.75 | 54 | 82.9 |
| 5 | 4.75 | 56 | 95.3 |
| 6 | 5.25 | 56 | 94.5 |
| 7 | 5.75 | 57 | 94.0 |
| 8 | 6.25 | 59 | 90.3 |
| 9 | 6.75 | 60 | 91.7 |
| 10 | 7.25 | 59 | 91.7 |

EXAMPLE IX

Addition of H$_2$S to Acrylonitrile

The reaction of H$_2$S with acrylonitrile under the conditions used with the acrylate esters was established. The reaction was very exothermic and required more cooling than provided by the equipment used. Rapid secondary reaction to the sulfide led to greatly reduced selectivity tot he mercaptan.

TABLE X

Addition of H$_2$S to Acrylonitrile
Pressure: 450 Psig
Conversion: 100%

| Run No. | Total Run Time, Hrs. | LHSV (hr$^{-1}$) | H$_2$S/Nitrile Molar Ratio | Selectivity, % to Mercaptan |
|---|---|---|---|---|
| 1 | 1.67 | 6.02 | 6.07 | 43.9 |
| 2 | 5.25 | 13.70 | 15.8 | 24.7 |
| 3 | 5.8 | 15.14 | 17.6 | 27.7 |

What is claimed is:

1. A continuous process for the production of mercapto-substituted compounds which comprises passing a mixture of hydrogen sulfide and at least one olefinically unsaturated compound in which the double bond is conjugated with an activating group selected from the group consisting of carbonyl, carboxyl, carboxylate, carboxamide, nitrile, nitro and sulfoxide through a reaction zone comprising a bed of magnesium oxide catalyst which optionally contains silica or other suitable binding agent under reaction conditions which produce saturated sulfur compounds and separating excess hydrogen sulfide from the product mixture removed from said reaction zone.

2. A process according to claim 1 wherein methyl acrylate is converted to methyl 3-mercaptopropionate.

3. A process according to claim 1 wherein the mole ratio of hydrogen sulfide to carboxylate ranges from about 3 to about 10 moles per mole, the temperature of contacting is in the range of about 25° C. to about 150° C., and the flow rate of reaction mixture through the catalyst bed ranges from about 1 to about 10 liquid hourly space velocity (LHSV).

4. A process according to claim 3 wherein methyl acrylate is converted to methyl 3-mercaptopropionate.

5. A process according to claim 1 wherein said activating group is selected from at least one of carbonyl, carboxyl, carboxamide, nitrile, nitro, and sulfoxide.

* * * * *